US00PP27152P3

(12) United States Plant Patent
Madsen

(10) Patent No.: US PP27,152 P3
(45) Date of Patent: Sep. 13, 2016

(54) ***SCHLUMBERGERA* PLANT NAMED 'PKMSCHL05'**

(50) Latin Name: ***Schlumbergera truncata* (Haworth) Moran hybr.**
Varietal Denomination: PKMSchl05

(71) Applicant: Gartneriet PKM A/S, Odense N (DK)

(72) Inventor: Christian Hald Madsen, Korsor (DK)

(73) Assignee: Gartneriet PKM A/S, Odense N (DK)

( * ) Notice: Subject to any disclaimer, the term of this patent is extended or adjusted under 35 U.S.C. 154(b) by 155 days.

(21) Appl. No.: 13/999,459

(22) Filed: Feb. 28, 2014

(65) Prior Publication Data

US 2015/0250083 P1 Sep. 3, 2015

(51) Int. Cl.
*A01H 5/02* (2006.01)

(52) U.S. Cl.
USPC ..... Plt./372

(58) Field of Classification Search
USPC ..... Plt./372
See application file for complete search history.

(56) References Cited

PUBLICATIONS

Printout of application information from Community Plant Variety Office (CPVO) website for correspoding CPVO application No. 2014/0090 filed Jan. 20, 2014 (1 page) (http://www.cpvoextranet.cpvo.europa.eu).

*Primary Examiner* — Keith Robinson
(74) *Attorney, Agent, or Firm* — Foley & Lardner LLP

(57) ABSTRACT

A new and distinct cultivar of *Schlumbergera truncata* (Haworth) Moran hybr. plant named 'PKMSchl05', characterized by its dense growth habit and white colored flowers. When grown at low temperatures the flowers are light pink (as shown in the figures).

6 Drawing Sheets

Latin name of the genus and species claimed: *Schlumbergera truncata* (Haworth) Moran hybr.

Variety denomination: 'PKMSchl05'.

BACKGROUND OF THE INVENTION

The present invention relates to a new and distinct cultivar of *Schlumbergera* plant, botanically known as *Schlumbergera truncata* (Haworth) Moran hybr., common name Christmas Cactus, and hereinafter referred to by the variety denomination 'PKMSchl05'.

The new *Schlumbergera* is a product of a planned breeding program conducted by the inventor in Søhus, Denmark. The new *Schlumbergera* originated from an outcrossing made in 2004 by the Inventor between two proprietary, unnamed cultivars of *Schlumbergera truncata* hybr. The Inventor selected the new *Schlumbergera* cultivar from the progeny of the above crossing in 2006 on the basis of its flower color and compact, freely branching habit. Plants of the new *Schlumbergera* are more upright and compact and thus better suited to production in 5.5 cm pots.

Asexual reproduction of the new cultivar by phylloclade cuttings taken and propagated and trial production batches in Søhus, Denmark, has shown that the unique features of this new *Schlumbergera* are stable and reproduce true to type in many successive generations.

BRIEF DESCRIPTION OF THE INVENTION

The following traits have been repeatedly observed and are determined to be the unique characteristics of 'PKMSchl05'. These characteristics in combination distinguish 'PKMSchl05' as a new and distinct cultivar:

1. Smaller phylloclades and flowers; and
2. Higher number of flowers and phylloclades per plant.

Plants of the cultivar 'PKMSchl05' can be compared to plants of the *Schlumbergera truncata* (Haworth) Moran hybr. cultivar 'Malissa' (unpatented). However, in side-by-side comparisons conducted over several seasons by the inventor in Søhus, Denmark, plants of the cultivar 'PKMSchl05' and the cultivar 'Malissa' differ in the following characteristics:

1. Plants of the new *Schlumbergera* have smaller and more phylloclades than plants of the cultivar 'Malissa'.
2. Plants of the new *Schlumbergera* have phylloclades with smaller teeth than plants of the cultivar 'Malissa'.
3. Plants of the new *Schlumbergera* have smaller and more flowers than plants of the cultivar 'Malissa'.

Data regarding the parent varieties is no longer available for comparison with the claimed variety.

BRIEF DESCRIPTION OF THE DRAWINGS

The accompanying colored photographs illustrate the overall appearance and details of flower form color and structures of the new cultivar, showing the colors as true as it is reasonably possible to obtain in colored reproductions of this type. Colors in the photographs may differ slightly from the color values cited in the detailed botanical description, which accurately describe the actual colors of the claimed variety. Plants in the photos are about 12 months old.

Photographs were taken after production at low temperatures (12° C.) for the final three weeks before the start of flowering and show the light pink flower color associated with the low temperature production. Production at higher, normal temperatures (18° C.) will yield almost entirely white flowers.

DETAILED BOTANICAL DESCRIPTION

Figure 1:
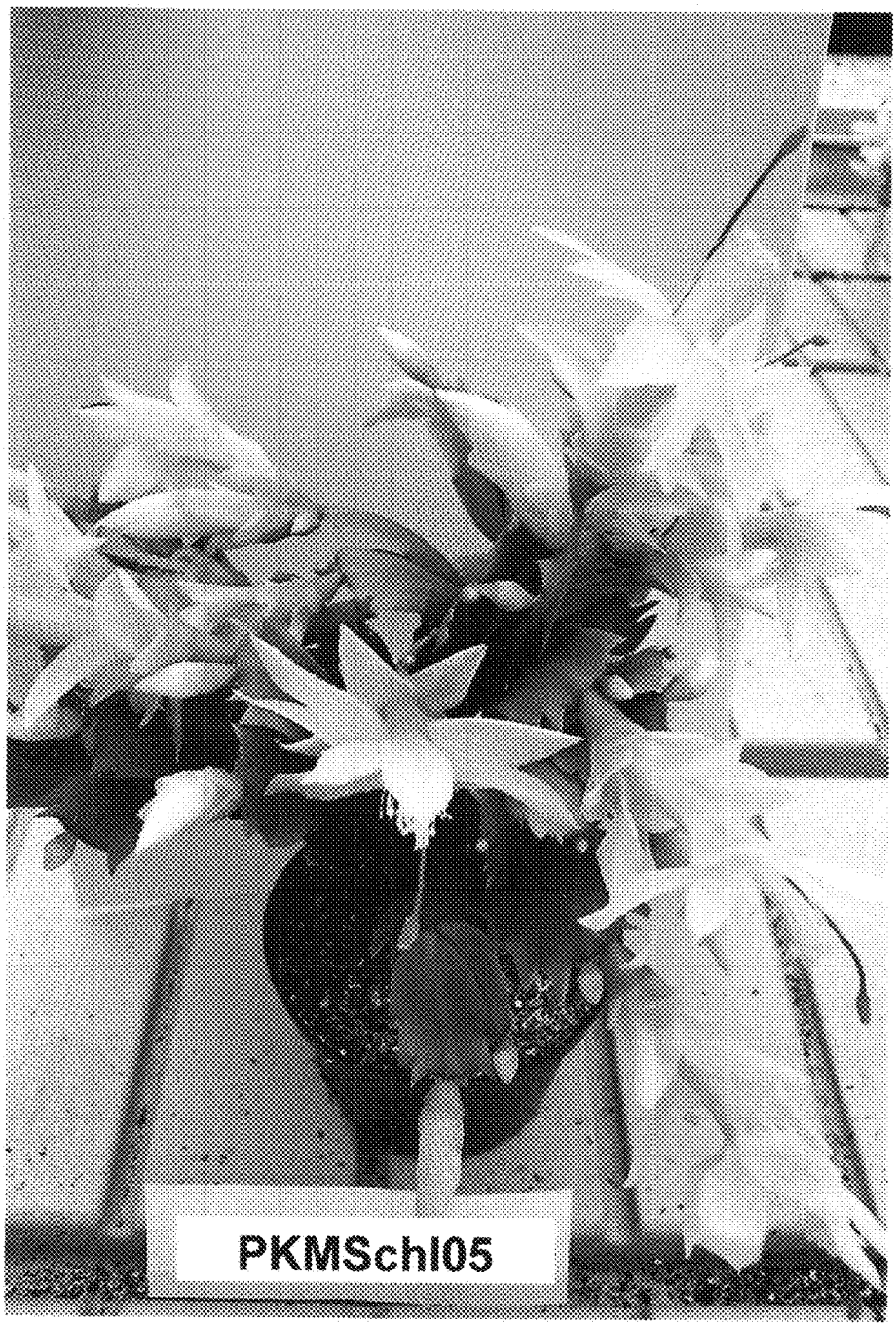
FIG. 1—shows a typical plant of 'PKMSchl05' as grown in a 5.5 cm pot.
Figure 2:
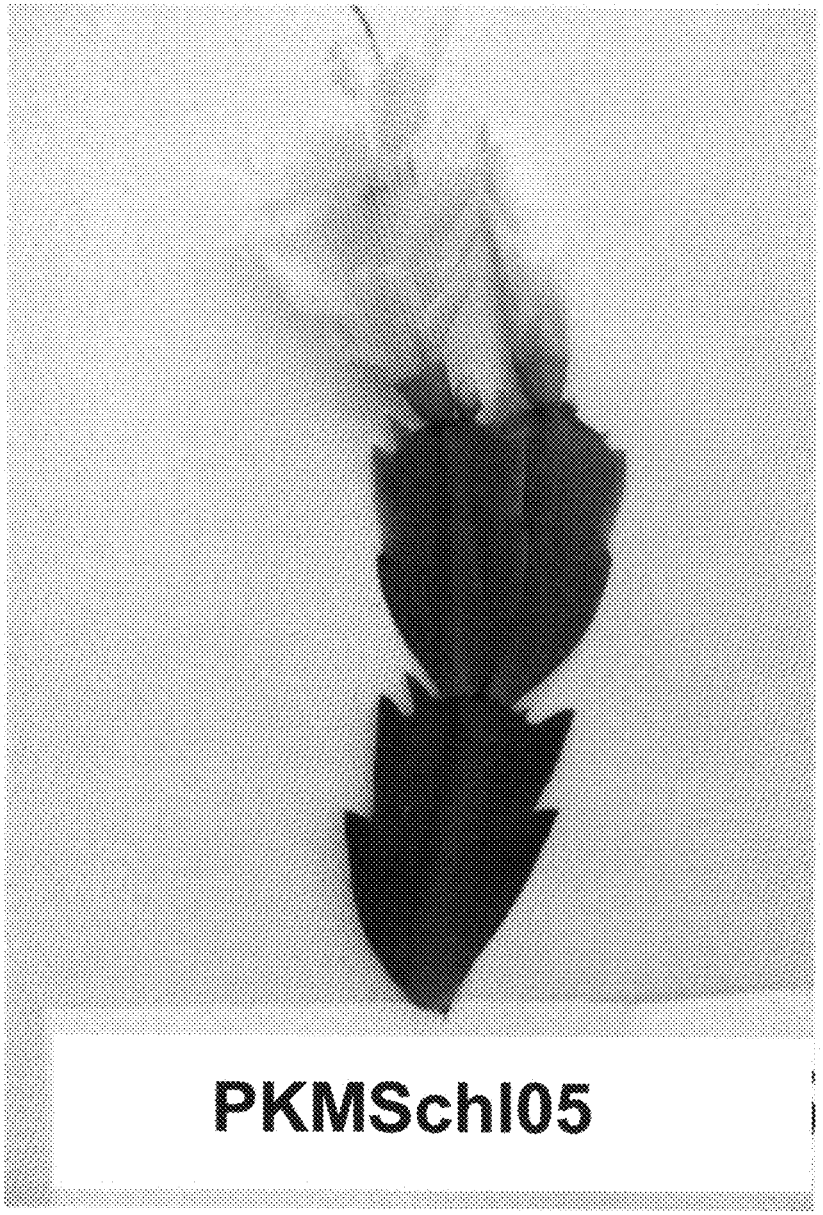
FIG. 2—shows a typical flower and phylloclade of 'PKMSchl05'.
Figure 3:
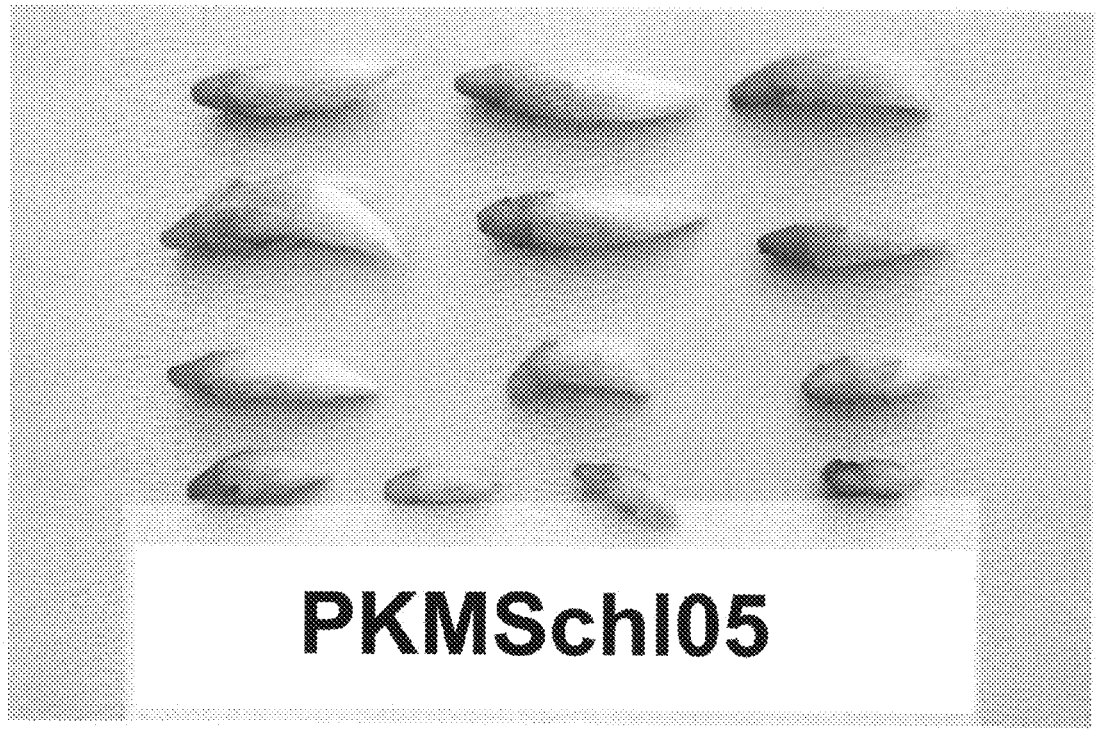
FIG. 3—shows typical buds of 'PKMSchl05'.
Figure 4:
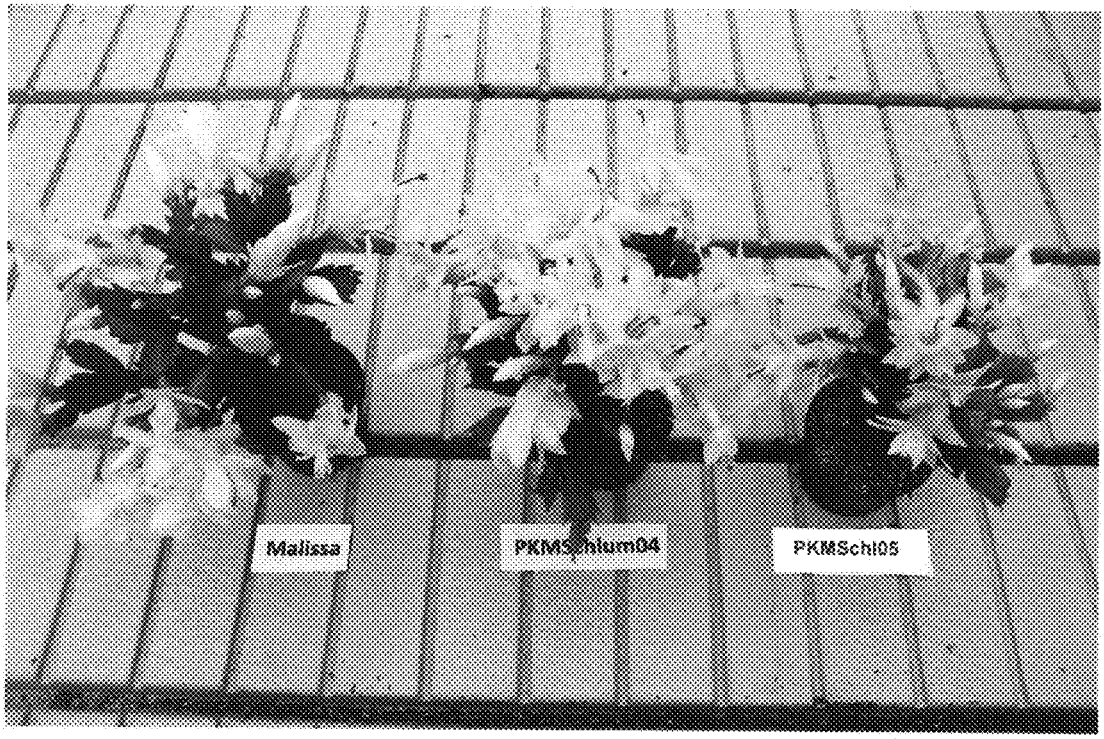
FIG. 4—shows a typical plant of 'PKMSchl05' in comparison with two other *Schlumbergera* varieties, as grown in 9 cm pots.
Figure 5:
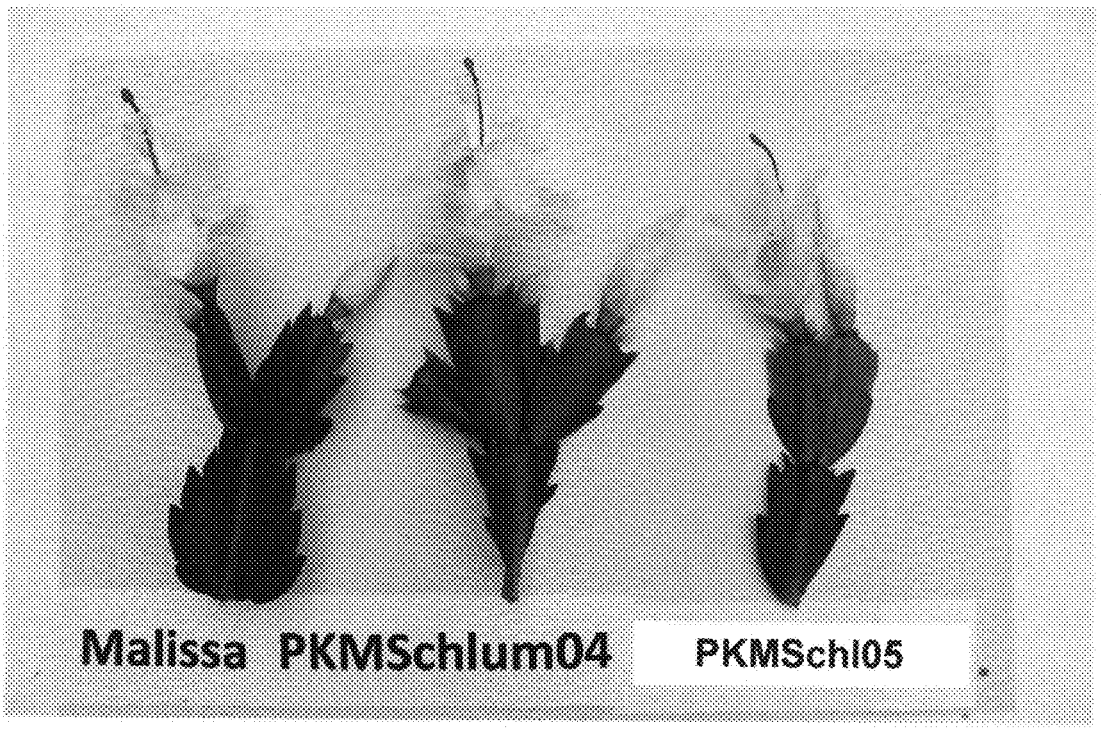
FIG. 5—shows a typical flower and phylloclade of 'PKMSchl05' in comparison with a typical flower and phylloclade from two other *Schlumbergera* varieties.
Figure 6:
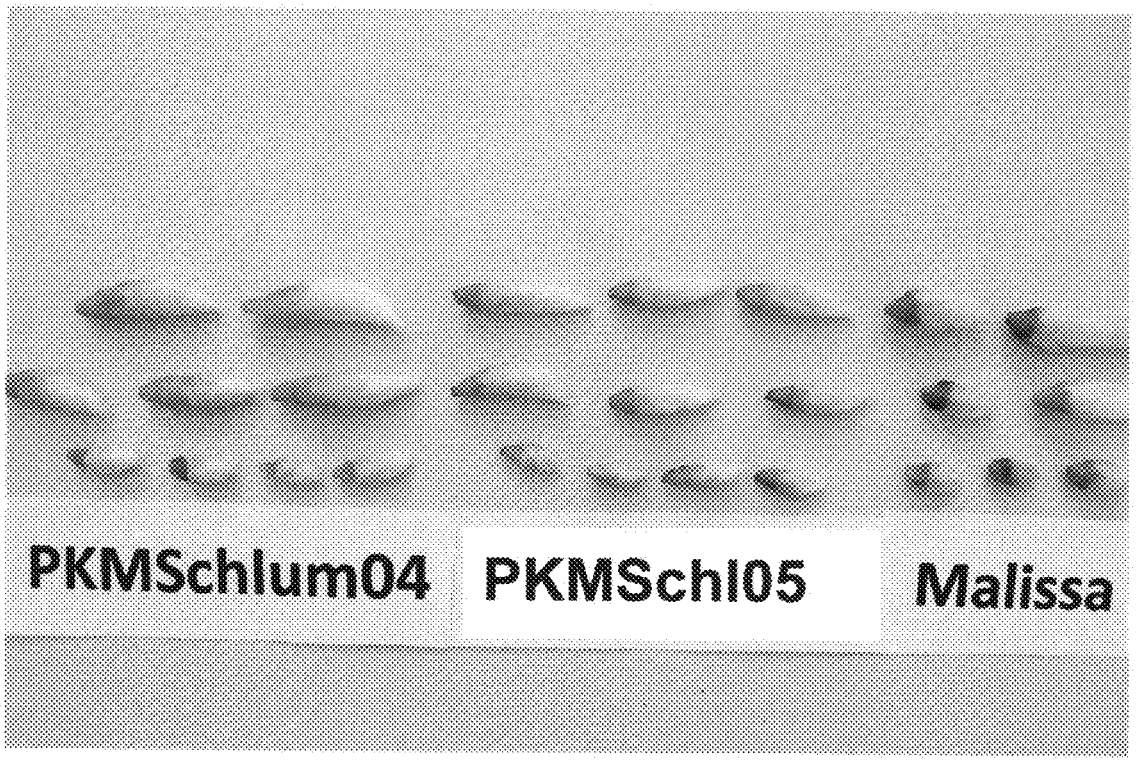
FIG. 6—shows typical buds of 'PKMSchl05' in comparison with typical buds from two other *Schlumbergera* varieties.

Plants of the cultivar 'PKMSchl05' have not been observed under all possible environmental conditions. The phenotype may vary somewhat with variations in environment such as temperature, light intensity, day length, and fertility level without, however, any variance in genotype.

In the following description, color references are made to The Royal Horticultural Society Colour Chart, 5$^{th}$ edition, where general terms of ordinary dictionary significance are used. Plants were grown under greenhouse conditions. Plants used for this description are about 12 months old.

Classification:

*Botanical.*—*Schlumbergera truncata* (Haworth) Moran hybr.

*Variety denomination.*—'PKMSchl05'.

Parentage:

*Female or seed parent.*—Proprietary selection of *Schlumbergera truncata* (Haworth) Moran hybr.

*Male or pollen parent.*—Proprietary selection of *Schlumbergera truncata* (Haworth) Moran hybr.

Propagation:

*Type cutting.*—Single mature phylloclades.

*Form.*—Perennial plant (epiphyte), plants have an upright shape and branched growth habit. Flowers singular, double, or triple at apical ends of terminal phylloclades. Freely branching with one to four new phylloclades forming at the apical ends of older phylloclades.

*Time to initiate roots.*—2-3 weeks at 21° C.

*Rooting habit.*—Fibrous, well-branched.

*Crop time.*—After rooting, about 12 months are required to produce finished flowering plants in 5.5 cm pots.

Plant:

*Plant height* (*soil level to top of plant,* 3 *levels of phylloclades, excl. flowers*).—12.5 cm.

*Vigor.*—Good.

*Growth rate.*—Slow.

*Plant spread.*—18-20 cm.

*Lateral branch length.*—(3 levels of phylloclades): 10 cm.

*Lateral branch width.*—2.5 to 3.0 cm.

*Lateral branch color.*—NN137A.

*Lateral branch texture.*—Glabrous, smooth.

*Lateral branch arrangement and aspect.*—Freely branching with one to three new phylloclades forming at apical ends of older phylloclades.

Phylloclades:

*Quantity per lateral branch.*—12-15.

*Length.*—4.0 to 4.5 cm.

*Width.*—2.5 to 3.0 cm.

*Thickness.*—Approximately 2 mm.

*Shape.*—Obovate.

*Apex.*—Truncate with 2 protruding marginal teeth, 3-4 mm in length. Barbellulate with 10-15 short bristles.

*Base.*—Rounded.

*Margin.*—Serrate, 2-4 teeth per phylloclade, 1-3 mm in length.

*Texture.*—Glabrous, smooth.

*Pubescence.*—None.

*Color.*—RHS NN137A, Green.

*Venation pattern.*—Costate.

*Venation color.*—RHS 144C, Yellow-Green.

Inflorescence:

*Blooming season.*—October to December in the Northern hemisphere. Can be changed with short day treatments. Flowers appear 8-9 weeks after end of short day treatment.

*Longevity on plant.*—Highly dependent on temperature and light conditions; generally 5 to 6 days. Flowers are persistent.

*Buds.*—Aspect: Upright to outward. Number: 1-3 buds per lateral branch. Length: Up to 3 cm before unfolding of tepals. Diameter: Up to 1 cm before unfolding of tepals. Shape: Ovoid to lanceolatoid. Color: RHS 4D, yellow in small (~1 cm) buds; RHS 55C, red at tips and RHS 155D, white at base in larger (~3 cm) buds. Buds changing from white to pink with increasing bud size when grown at 12° C.

*Flowers.*—Arrangement: 1-3 sessile flowers on apical phylloclades (per lateral branch). Shape and form: Zygomorphic; tubular with lobes (tepals) extruding at base and at tube end. Fragrance: None. Tepal Arrangement: Inner whorl of tepals fused to form a tube. Corolla tepals are initially at right angle to tube, later somewhat reflexed. Tepal Number: 10 in fused inner whorl forming the tube; 5-7 more or less free tepals in outer whorl. Tepal Shape: Narrow Ovate. Tepal Apex: Apiculate. Tepal Margin: Entire. Tepal Length: 20-25 mm. Tepal Width: 10 mm. Tube Diameter: 10-12 mm. Flower Diameter: 5 cm. Tube Depth: 3.5 cm. Tube shape: Tubular. Flower Depth: 6.0 cm. Texture: Silky. Color: When opening, upper side: lobes RHS NN155D, White. When opening, under side: lobes RHS NN155D, White. Fully opened, upper side: lobes RHS NN155D, White. Fully opened, under side: lobes RHS NN155D, White; tube N66C, red-purple when grown at 12° C. for last 3 weeks before flowering. At higher, normal temperatures (18° C.), flowers are almost completely white RHS NN155D. A pinkish-purple diffuse ring is present at the upper end of the tube (color almost as the stigma, RHS 61B). Tepal color fading: No fading.

Reproductive organs:

*Stamen.*—Number: Many (80-100 per flower), polyandrous, phaneranherous. Shape: Incurved. Some filaments fused to perianth tube (connate). Color: RHS 11C, yellow.

*Anther.*—Shape: Basifixed; ovoid. Color: RHS 11C, yellow. Length: 1-2 mm. Pollen: Plenty; color RHS 11D yellow.

*Filament.*—Length: 4-5 cm. Color: RHS 155D, translucent white.

*Pistil.*—Number: 1. Length: 55 mm. Shape: Slightly curved.

*Stigma.*—Shape: Claw-like. Color: RHS 61B, red-purple.

*Style.*—Color: RHS N66A, red-purple. Length: 55 mm.

*Ovary.*—Color: RHS 144C, yellow green. Length: 9-11 mm. Width: 8-10 mm. Shape: Obovate to turbinate; can have 4 small wings.

Seeds: None observed.

Weather tolerance: Tolerant to a high temperature of 40° C. and a low temperature of 2° C.

Disease/pest resistance: Not tested.

What is claimed is:

1. A new and distinct cultivar of *Schlumbergera* plant named 'PKMSchl05', as illustrated and described herein.

* * * * *